United States Patent [19]
Ho et al.

[11] Patent Number: 5,753,465
[45] Date of Patent: May 19, 1998

[54] UNMODIFIED RECOMBINANT HUMAN ADULT HEMOGLOBIN PRODUCTION

[75] Inventors: Chien Ho; Tong-Jian Shen, both of Pittsburgh, Pa.

[73] Assignee: Carnegie Mellon University, Pittsburgh, Pa.

[21] Appl. No.: 298,339

[22] Filed: Aug. 30, 1994

[51] Int. Cl.$^6$ .......................... C12P 21/02; C12N 15/63; C07K 14/805
[52] U.S. Cl. .................. 435/69.6; 435/320.1; 530/385
[58] Field of Search ........................ 435/69.1, 320.1, 435/69.6

[56] References Cited

U.S. PATENT DOCUMENTS

| | | | |
|---|---|---|---|
| 4,865,974 | 9/1989 | Ben-Bassat, et al. | 435/68 |
| 4,870,017 | 9/1989 | Ben-Bassat, et al. | 435/212 |
| 5,013,662 | 5/1991 | Ben-Bassat et al. | 435/212 |

OTHER PUBLICATIONS

Peterson, D. et al (1994) "In vivo enhancement of N-terminal processing of recombinant human proteins in E. coli" Abstr. Gen. Meet. Am. Soc. Microbiol. May 23–27, 1994, Las Vegas, Nevada, 357.

Misoka F. (1991) "Production using genetic engineering. Protease production in E. coli" Nagasaki-ken Kogyo Gitjutsu Senta Kenkyu Hokoku. 8:115–118,1991.

Mulder, A.G., et al., *J. Cell. Comp. Physiol.* 5:383 (1934).

Bunn, H.F., et al., *J. Exp. Med.* 129:909 (1969).

Chada, K., et al., *Nature (London)* 314:377 (1985).

Townes, T.M., et al., *EMBO J.* 4:1715 (1985).

Swanson, M.E., et al., *Bio/Technology* 10:557 (1992).

Groebe, D.R., et al., *Protein Expression and Purification* 3:134 (1992).

Wagenbach, M., et al., *Bio/Technology* 9:57 (1991).

DeLlano, J.J., et al., *Proc. Natl. Acad. Sci. USA* 90:918 (1993).

Hoffman, S.J., et al., *Proc. Natl. Acad. Sci. USA* 87:8521 (1990).

Hernan, R.A., et al., *Biochemistry* 31:8619 (1992).

Nagai, K., et al., *Nature (London)* 309:810 (1984).

Nagai, K., et al, *Methods Enzymol.* 153:461 (1987).

Bunn, H.F., et al., *Hemoglobin: Molecular, Genetic and Clinical Aspects* (Saunders, Philadelphia) pp. 37–60 (1986).

Kavanaugh, J.S., et al., *Biochemistry* 31:8640 (1992).

Ben–Bassat, A., et al., *J. Bacteriol.* 169:751 (1987).

Hirel, P.H., et al., *Proc. Nat. Acad. Sci. USA* 86:8247 (1989).

Miller, J.H., et al., *Experiments in Molecular Genetics*, Cold Springs Harbor Lab Press, Plainview, NY (1972).

Antonini, E., et al., *Hemoglobin and Myglobin in Their Reactions with Ligands* (North Holland, Amsterdam) p. 19 (1971).

Bucci, E., *Methods Enzymol.* 76:97 (1981).

Waks, M., et al., *J. Biol. Chem.* 248:6462 (1973).

Lindstrom, T.R., et al., *Proc. Natl. Acad. Sci. USA* 69:1707 (1972).

Hewick, R.M., et al., *J. Biol. Chem.* 256:7990 (1981).

*Pure Appl. Chem.* 63:975 (1991).

Bunn H.F., et al., *Hemoglobin: Molecular, Genetic and Clinical Aspects* (Sanders, Philadelphia) pp. 634–662 (1986).

Plateau, P., et al., *J. Am. Chem. Soc.* 104:7310 (1982).

(List continued on next page.)

*Primary Examiner*—Robert A. Wax
*Assistant Examiner*—Kawai Lau
*Attorney, Agent, or Firm*—Reed Smith Shaw & McClay LLP

[57] ABSTRACT

Methods for obtaining unmodified recombinant human normal adult hemoglobin involve a novel expression plasmid that coexpresses human α- and β-globin genes and *E. coli* methionine aminopeptidase genes under the control of separate tac promoters. Methods are also provided for correcting an abnormal conformation of some of the heme groups incorporated in the proteins expressed by the expression plasmid.

9 Claims, 10 Drawing Sheets

OTHER PUBLICATIONS

Hayashi, A., et al., *Biochem. Biophys. Acta* 310:309 (1973).

Ho, C., *Adv. Protein Chem.* 43:153 (1992).

Takashi, S., et al., *Biochemistry* 19:5196 (1980).

Fung, L.W–M., et al., *Biochemistry* 14:2526 (1975).

La Mar, G.N., et al., *Biochem. Biophys. Res. Commun.* 96:1172 (1980).

Shen, T.–J. et al. (1993) "Production of unmodified human adult hemoglobin in *Escherichia coli* " *Proc. Nat'l Acad. Sci., USA* 90(17):8108–8112.

La Mar, G.N. et al. (1985) "$^1$H NMR characterization of metastable and equilibrium heme orientational heterogenity in reconstituted and native human hemoglobin" *Biochem.* 24:3826–3831.

Hoffman, S.J. et al. (1990) "Expression of fully functional tetrameric human hemoglobin in *Escherichia coli*" *Proc. Nat'l Acad. Sci., USA* 87:8521–8525.

Ben–Bassat, A. et al. (1987) "Processing of the initiation methionine from proteins: properties of the *Escherichia coli* methionine aminipeptidase and its gene structure" *J. Bact.* 169(2):751–757.

Ishimori, K. et al. (1988) "Study of the specific heme orientation in reconstituted hemoglobins" *Biochem.* 27:4747–4753.

Yamamoto, Y. et al. (1986) "$^1$H NMR study of dynamics and thermodynamics of heme rotational disorder in native and reconstituted hemoglobin A" *Biochem.* 25:5288–5297.

Human $Fe^{+3}$-Hb A

Recombinant $Fe^{+3}$-Hb A (Peak b)

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 29 nucleotides
        ( B ) TYPE: nucleic acid
        ( C ) STRANDEDNESS: single
        ( D ) TOPOLOGY: linear ( i i ) MOLECULE TYPE: Synthetic DNA ( x ) PUBLICATION INFORMATION:
        ( A ) AUTHORS: Tong-Jian Shen
                Nancy T. Ho
                Virgil Simplaceanu
                Ming Zou
                Brian N. Green
                Ming F. Tam
                Chien Ho
        ( B ) TITLE: Production of unmodified human adult hemoglobin
            in Escherichia coli
        ( C ) JOURNAL: Proc. Natl. Acad. Sci. USA
        ( D ) VOLUME: 90
        ( E ) ISSUE: None
        ( F ) PAGES: 8108-8112
        ( G ) DATE: 00-SEP-93
        ( K ) RELEVANT RESIDUES IN SEQ ID NO: 1: 1 to 29

( x i ) SEQUENCE DESCRIPTION: SEQ ID NO: 1:

TGGACAGAAT TCCATGGCTA TCTCAATCA                      29

( 2 ) INFORMATION FOR SEQ ID NO:2:

( i ) SEQUENCE CHARACTERISTICS:
        ( A ) LENGTH: 26 nucleotides
        ( B ) TYPE: nucleic acid
        ( C ) STRANDEDNESS: single
        ( D ) TOPOLOGY: linear ( i i ) MOLECULE TYPE: Synthetic DNA ( x ) PUBLICATION INFORMATION:
        ( A ) AUTHORS: Tong-Jian Shen
                Nancy T. Ho
                Virgil Simplaceanu
                Ming Zou
                Brian N. Green
                Ming F. Tam
                Chien Ho
        ( B ) TITLE: Production of unmodified human adult hemoglobin
            in Escherichia coli
        ( C ) JOURNAL: Proc. Natl. Acad. Sci. USA
        ( D ) VOLUME: 90
        ( E ) ISSUE: None
        ( F ) PAGES: 8108-8112
        ( G ) DATE: 00-SEP-93

( x i ) SEQUENCE DESCRIPTION: SEQ ID NO: 2:

TGGCTTAAGC TTATTCGTCG TGCGAG                        26

UNMODIFIED RECOMBINANT HUMAN ADULT HEMOGLOBIN PRODUCTION

ACKNOWLEDGMENT

The present invention was developed in part with government support under grant number HL-24525 awarded by the National Institutes of Health. The government has certain rights in this invention.

FIELD OF THE INVENTION

The present invention relates generally to production of human normal adult hemoglobin ("Hb A") and more particularly relates to production of recombinant human normal adult hemoglobin ("rHb A") that is unmodified, and possessing biological functionality essentially identical with native human normal adult hemoglobin. A method is included for correcting an abnormal conformation of some of the heme groups incorporated in the expressed proteins.

BACKGROUND OF THE INVENTION

The prevalence of infectious agents such as HIV and hepatitis in red blood cells of human blood products coupled with blood shortages from lack of suitable donors and over demand for blood, has led to great interest in the development of red cell substitutes, particularly human hemoglobin ("Hb") and its derivatives. Hb is the oxygen-carrying component of blood, circulated through the blood stream inside erythrocytes (red blood cells).

Hb A is a tetrameric protein containing two α chains having 141 amino acid residues each and two β chains having 146 amino acid residues each, and also bearing prosthetic groups known as hemes. The erythrocytes help maintain hemoglobin in its reduced, functional form. The heme-iron atom is susceptible to oxidation, but may be reduced again by one of two systems within the erythrocyte, the cytochrome $b_5$, and glutathione reduction system.

The use of cell-free solutions of Hb as a potential oxygen-carrying red cell substitute has been investigated for a long time. See, for example, Mulder, A.G., et al., *J. Cell Comp. Physiol.* 5:383 (1934), the disclosure of which is incorporated herein by reference. The use of unmodified cell-free human Hb purified from red blood cells suffers from several limitations in addition to contamination and supply limitations noted above: increase in oxygen affinity due to loss of the cofactor 2,3-bis (phospho) glycerate; and dissociation of Hb tetramers into αβ dimers which are cleared by renal filtration and which can cause long-term kidney damage. See, for example, Bunn, H. F., et al., *J. Exp. Med.* 129:909 (1969), the disclosure of which is incorporated herein by reference.

Human globins and Hbs have been expressed in the following: transgenic mice, see, for example, Chada, K., et al., *Nature (London)* 314:377 (1985) and Townes, T. M., et al., *EMBO J.* 4:1715 (1985), the disclosures of which are incorporated herein by reference; transgenic swine as described by Swanson, M. E., et al., *Bio/Technology* 10:557 (1992), the disclosure of which is incorporated herein by reference; insect cell cultures as reported by Groebe, D. R., et al., *Protein Expression and Purification* 3:134 (1992), the disclosure of which is incorporated herein by reference; yeast as described by Wagenbach, M., et al., *Bio/Technology* 9:57 (1991) and DeLiano, J. J., et al., *Proc. Natl. Acad. Sci. USA* 90:918 (1993), the disclosures of which are incorporated herein by reference and Escherichia coli ("*E. coli*") as described by Hoffman, S. J., et al., *Proc. Natl. Acad. Sci. USA* 87:8521 (1990) and Hernan, R. A., et al., *Biochemistry* 31:8619 (1992), the disclosures of which are incorporated herein by reference. In many respects, the *E. coli* system is the best choice for such purposes because of its high expression efficiency and the ease of performing site-directed mutagenesis.

The first *E. coli* system to express human α- or β-globin as a fusion protein was developed as described by Nagai, K., et al., *Nature (London)* 309:810 (1984) and Nagai, K., et al., *Methods Enzymol.* 153:461 (1987), the disclosures of which are incorporated herein by reference, but the product processing procedure is very laborious and gives a low yield. Thus, this expression system is not desirable, especially when large amounts of recombinant Hb ("rHb") are required for biochemical, biophysical, and biological studies.

Hoffman, S. J., et al., *Proc. Natl. Acad. Sci. USA* 87:8521 (1990) have reported a coexpression system in which the synthetic human α- and β-globin genes are organized in a single cistron and are expressed in equal amounts. Both of the expressed α- and β-globins are properly assembled with endogenous hemes into tetrameric Hb molecules in *E. coli*. Hernan, R. A., et al., *Biochemistry* 31:8619 (1992) have reported the expression of a nonfusion single β-globin in *E. coli*. Although these two nonfusion systems work very well in several aspects, an extra methionine residue is retained at the amino (N)-termini of both α- and β-globins.

The natural N-terminal valine residues of Hb A are known to play important roles in regulating oxygen affinity, the Bohr effect, and interactions with allosteric effectors and anions as reported by Bunn, H. F., et al., *Hemoglobin: Molecular, Genetic and Clinical Aspects* (Saunders, Philadelphia) pp. 37–60 (1986), the disclosure of which is incorporated herein by reference. The extra methionine can alter the N-terminal conformation of the Hb molecule as reported by Kavanaugh, J. S., et al., *Biochemistry* 31:8640 (1992), the disclosure of which is incorporated herein by reference. Hence, the oxygenation properties of Hb depend on the integrity of the N-terminal residue thereby mandating the removal of the extra methionine residues from the N-termini of both α- and β-globins of the expressed Hb before the *E. coli* system can be used effectively for the production of desired unmodified and mutant Hbs.

Methionine aminopeptidase ("Met-AP" or "MAP") has been found to be responsible for the removal of the N-terminal methionine residue from a nascent peptide chain in *E. coli*, Salmonella, Bacillus, and yeast, and the Met-APs from a variety of organisms have been purified and characterized. See, for example, Ben-Bassat, A., et al., *J. Bacteriol.* 169:751 (1987) and U.S. Pat. Nos. 4,865,974, 4,870,017, and 5,013,662, the disclosures of which are incorporated herein by reference. These enzymes possess unique specificity for the N-terminal methionine of a peptide or a protein, and the Met-APs of *E. coli* and *Salmonella typhimurium* have been reported to remove the N-terminal methionine from a number of expressed foreign proteins. Id.

There remains a need, however, for methods to recombinantly produce Hb A that is unmodified, that is, without N-terminal methionines and with its heme groups in their proper conformation for use as a component of a blood substitute or therapeutic agent. There is a further need for an efficient expression system producing unmodified rHb A in high yield that can also be used to produce mutant Hbs that are desired for therapeutic uses.

SUMMARY OF THE INVENTION

Accordingly, it is a primary object of the present invention to provide an expression system for producing unmodified rHb A, that is, without N-terminal methionines.

Another object of the present invention is to provide an efficient expression system for producing unmodified rHb A.

Yet another object of the present invention is to provide a method of producing unmodified rHb A that possesses biological functionality essentially identical with native human adult hemoglobin.

Yet another object of the present invention is to provide methods for correcting the abnormal conformation of the heme groups in the β subunits of unmodified rHb A to the correct conformation.

These and other objects of the present invention are achieved by one or more of the following embodiments.

In one aspect, the invention features a method for producing recombinant human normal adult hemoglobin (rHb A) that has the same amino acid sequence and heme conformation as native Hb A, comprising:

growing recombinant cells in a growth medium, the cells being a microorganism or cell culture transformed with an expression vector containing DNA encoding human α- and β-globin genes and the Met-AP gene under the control of separate tac promoters;

simultaneously expressing the DNA, thereby producing recombinant hemoglobins that are substantially free of N-terminal methionine;

thereafter purifying the recombinant hemoglobins to obtain two major rHb A components wherein the rHb A of the first component has essentially the same structural and functional properties as those of native Hb A, except that the β subunit of the rHb A contains between about 5 to 10% of amino-terminal methionine residues resulting from the expression and the rHb A of the second component has the same amino acid composition as native Hb A, but whose structural and functional properties differ from those of native Hb A; and converting the heme group conformation of the Hb A that comprises the second component to the native heme group conformation.

In a preferred embodiment, the conversion of the heme group of the second component is carried out by oxidizing the heme-iron atoms in the rHb A from $Fe^{+2}$ to $Fe^{+3}$, followed thereafter by reducing the oxidized heme-iron atoms in the rHb A from $Fe^{+3}$ to $Fe^{+2}$.

In another aspect, the invention features a recombinant DNA expression plasmid, comprising expressible human α- and β-globin genes and Met-AP gene from *E. coli* arranged in tandem under the control of separate tac promoters, the sequences being expressed separately for the human α- and β-globin genes and the Met-AP gene and incorporating heme to form rHb A with essentially the same amino acid sequence and heme conformation as native Hb A after oxidation and reduction of the second rHb A component obtained by fast protein liquid chromatography of the rHb A expressed by said plasmid.

Other features and advantages of the invention will be apparent from the following description of the preferred embodiment, and from the claims.

DESCRIPTION OF THE DRAWINGS

FIG. 4A is native Hb A; FIG. 4B is rHb A from peak a. FIG. 4C is rHb A from peak b.

DETAILED DESCRIPTION OF THE INVENTION

I. DEFINITIONS

Figure 1:
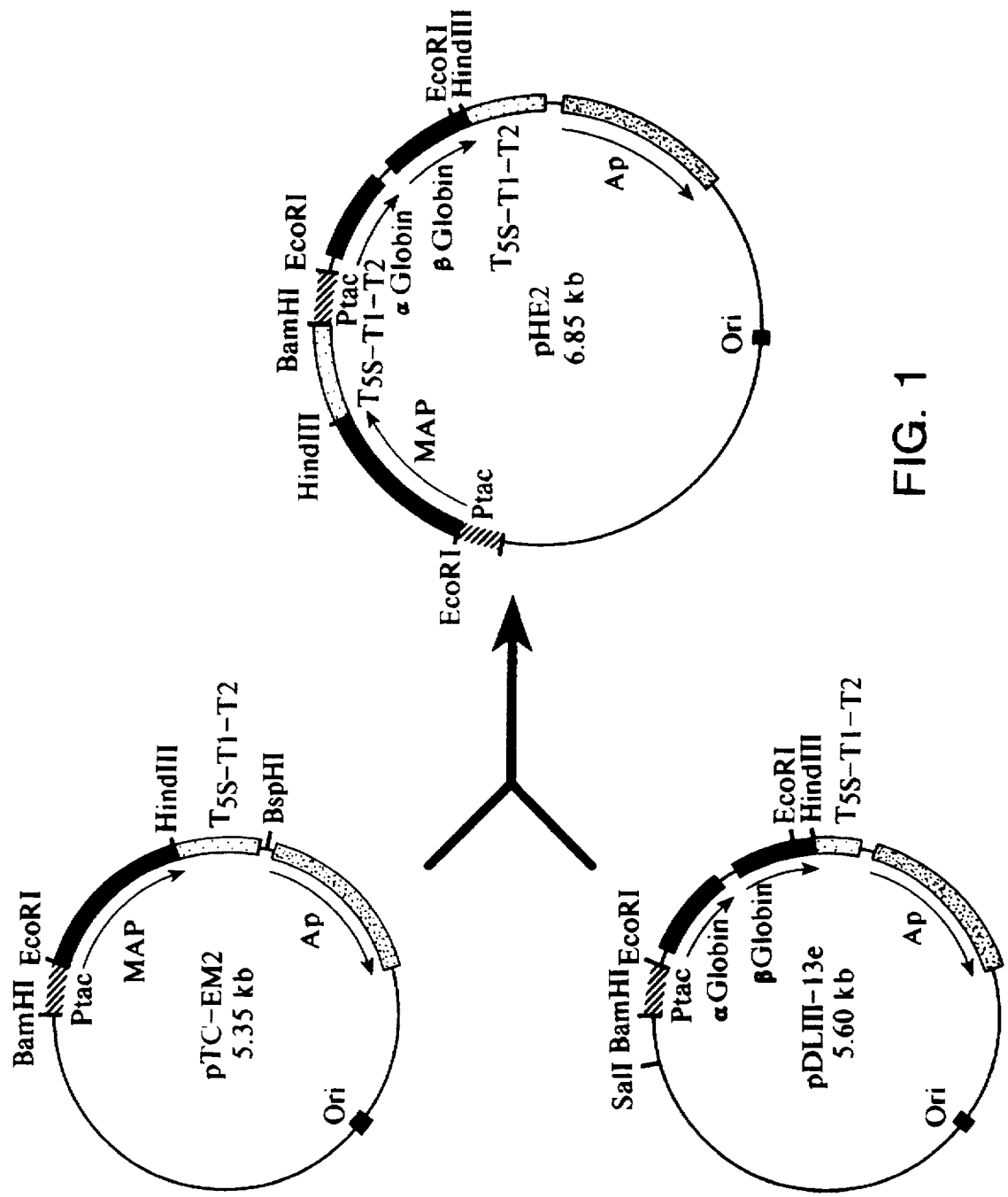
FIG. 1 shows the construction of plasmid pHE2 containing human α-and β-globin genes and the *E. coli* MAP gene for the production of unmodified rHb A in *E. coli*. "Ptac" means tac promoter, "Ap" means β-lactamase gene, "Ori" means origin of replication, and "$T_{5S-T1-T2}$" means5ST1T2 terminator.

As used herein, "Hb A" or "native Hb A" means human normal adult hemoglobin as obtained from human subjects.

"Recombinant human normal adult hemoglobin," "rHb A," and "unmodified rHb A" means human normal adult hemoglobin produced through recombinant DNA technology and having essentially the same structure and function as native Hb A.

"Deoxy" and "oxy" refer to the oxygenation state of the heme-iron atom in Hb A and rHb A. Oxyhemoglobin "Oxy-Hb" or "$HbO_2$" has four oxygen molecules bound to the heme groups; deoxyhemoglobin ("deoxy-Hb") contains no oxygen molecules. In normal arterial blood normal adult hemoglobin A ("Hb A") is in the oxy form ("oxy-Hb A"). In venous blood a portion of Hb A is in the deoxy form ("deoxy-Hb A").

"Ferri-hemoglobin," "ferri-Hb," "ferric form" "methemoglobin," "met-Hb", and "$Fe^{+3}$ state" all refer to Hb A or rHb A with its heme-iron atoms oxidized to the ferric ($Fe^{3+}$) state. Ferri-Hb does not bind oxygen.

"Ferro-hemoglobin," "ferro-Hb," "$Fe^{+2}$ state", and "ferrous form" refer to Hb A, rHb A, HbCO A and rHbCO A with its heme-iron atoms in the native, reduced ferrous ($Fe^{+2}$) state. Ferro-Hb is capable of binding oxygen or carbon monoxide.

"Carbonmonoxy-Hb" "HbCO A," "rHBCO A" and "CO form" all refer to hemoglobin bound to carbon monoxide molecules rather than oxygen molecules.

"Control" means a gene coding sequence being subject to another gene in the control region of a DNA molecule, in particular, a promoter, whereby the coding sequence can be expressed and regulated under the control of the promoter. Absent such control, the coding sequences may be expressed at too high or too low a level in the host organism, or at an improper time.

"Met-aminopeptidase," "Met-AP," and "MAP" refer to the enzyme methionine aminopeptidase which specifically cleaves the amino-(N) terminal methionine residue from a peptide sequence.

II. METHODS

According to the present invention, methods are provided for synthesizing unmodified rHb A, which has properties which are essentially identical to those of native Hb A. Hb A is the essential component in red blood cells due to its oxygen carrying function. Derivatives of Hb A that have a lower oxygen affinity than Hb A itself will find use in blood substitutes and components thereof. Moreover, unmodified rHb A and the *E. coli* expression system that is described herein that produces it are useful to produce mutants of Hb A that have particular properties via site-directed mutagenesis, such as, for example, altered oxygen affinity and altered cooperativity of oxygen binding. Additionally, the expression system of the present invention can be used to produce rHbs with mutations that compensate for mutants that are naturally occurring. Such resulting multiple mutants possess properties that compensate for the functional defect of the naturally occurring mutant.

Plasmid pHE2 was constructed in which synthetic human α- and β-globin genes are coexpressed with the *E. coli* MAP gene under the control of separate tac promoters. As will be shown, *E. coli* cells transformed with this plasmid express rHb A from which the N-terminal methionines have been effectively cleaved by the coexpressed MAP. The resulting rHb A is identical to native Hb A in a number of structural and functional properties. The production of unmodified rHb A will allow the production of a wide variety of mutants variously modified by resultant single or multiple amino acid substitutions, deletions, additions or replacements, for example by means of site-directed mutagenesis of the underlying DNA. Such resulting mutants will be useful for conventional therapy as well as for gene therapy.

However, it should be readily apparent that the methods of the present invention are not limited to production of rHb A. Indeed, the present invention may be practiced with other proteins that contain prosthetic groups such as, for example, heme, FAD, FMN, NADH, etc. Also, other expression systems in addition to *E. coli* can be used according to the present invention such as, for example, Salmonella, Bacillus, and yeast.

In the following example, a plasmid (pHE2) was constructed which coexpresses synthetic human α- and β-globin genes and the Met-AP gene from *E. coli* under the control of separate tac promoters. The rHbs were expressed in *E. coli* JM109, purified by fast protein liquid chromatography ("FPLC") and analyzed.

The N-terminal sequences of human α- and β-globins are Met-Val-Leu and Met-Val-His, respectively, and the N-terminal methionines before valine are not always removed even from some *E. coli* proteins under physiological levels of MAP (for example, see, Hirel, P.-H., et al., *Proc. Nat. Acad. Sci. USA* 86 :8247 (1989), the disclosure of which is incorporated herein by reference). Thus, a strong or excess overproduction of *E. coli* MAP is needed to remove N-terminal methionines from the expressed α- and β-globins. This is accomplished by separately placing the human α- and β-globin genes and MAP gene from *E. coli* under a strong tac promoter as well as putting these two expression cassettes into one plasmid, pHE2. Such a construction of plasmid pHE2 ensures almost the same copy number of human α- and β-globin genes and *E. coli* MAP gene, thus resulting in a strong overproduction of *E. coli* MAP, in any host cells. This arrangement is more advantageous than prior methods using two plasmids with two different origins of replication and the *E. coli* MAP gene with its congenital promoter. See, for example, U.S. Pat. Nos. 4,865,974, 4,870,017, and 5,013,662.

Example

Construction of Plasmid pHE2

Plasmid pHE2 was constructed in which the synthetic human α- and β-globin genes and the Met-AP gene from *E. coli* are arranged in tandem in the same orientation and are coexpressed under the control of separate tac promoters. The construction of pHE2 is diagrammatically shown in FIG. 1.

The *E. coli* Met-AP expression plasmid pTC-EM2 was constructed as follows. The coding sequence of the *E. coli* Met-AP gene was obtained by performing polymerase chain reaction ("PCR") using standard protocols with plasmid pSYC1174 (pSYC1174 in *E. coli* MM294 was a gift from Cetus Corp., Emeryville, Calif.; this strain also denoted *E. coli* strain pSYC1174 was also deposited with the American Type Culture Collection under accession number ATCC 53245 and is available to the public. See U.S. Pat. Nos. 4,865,974, 4,870,017, and 5,013,662) as the template and two synthesized primers, 5'-TGGACAGAATTCCATGGCTATCTCAATCA-3', SEQ. ID. NO:1 and 5'-TGGCTTAAGCTTATTCGTCGTGCGAG-3', SEQ. ID. NO:3. These primers are complementary to the 5' and 3'-end sequences of the *E. coli* Met-AP gene and contain an EcoRI site and a HindIII site, respectively. It should be readily apparent that the published coding sequence for the Met-AP gene disclosed in U.S. Pat. Nos. 4,865,974, 4,870,017 and 5,013,662 may also be used to obtain the equivalent starting product to that which was obtained using PCR methods and pSYC1174. The resulting PCR products were digested with these restriction enzymes and the resulting 0.8-Kb PCR product was inserted into the EcoRI and HindIII sites of the Hb A expression plasmid pDLIII-13e (a gift from Somatogen, Inc., Boulder, Colo., and fully disclosed in Hoffman, S. J., et al., *Proc. Natl. Acad. Sci. USA* 87: 8521 (1993), the disclosure of which is incorporated herein by reference). The resulting plasmid, pTC-EM2, contains the complete coding sequence of the *E. coli* Met-AP gene flanked by the tac promoter and 5ST1T2 terminators from pDLIII-13e.

In order to construct the plasmid that coexpressed *E. coli* Met-AP and unmodified rHb A, plasmid pDLIII-13e was first digested with BamHI. The cohesive end of the resulting cut plasmid was filled in with deoxynucleotide triphosphates ("dNTP's") (Boehringer Mannheim, Indianapolis, Ind.) and the Klenow fragment of DNA polymerase I (New England, Biolabs, Boston, Mass.) using standard methods. The resulting plasmid was then digested with SalI and then was partially filled in with dCTP and dTTP and the Klenow fragment to obtain a 5.3-Kb product. Plasmid pTC-EM2 was then first digested with BspHI, and then the cohesive end was filled in with dNTP's and the Klenow fragment. The plasmid was next digested with BamHI and then partially filled in with dATP and dGTP and the Klenow fragment to obtain a 1.5-Kb product.

The so obtained 5.3-Kb and 1.5-Kb fragments were then ligated to form the plasmid pHE2, the coexpression plasmid that contains the two expression cassettes arranged in tandem in the same orientation as follows: (1) tac promoter—*E. coli* Met-AP coding sequence—5ST1T2 terminator and (2) tac promoter-α-globin coding sequence-β-globin coding sequence-5ST1T2 terminator, as shown in FIG. 1. The beta-lactamase gene and replication of origin are from pDLIII-13e, which was based on pKK223-3 (Pharmacia Biotech, Inc., Piscataway, N.J.).

Coexpresson of Hb A Tetramer with *E. coli* Met-AP

*E. Coli* JM109 (Promega, Madison, Wis.) cells were grown in 2x YT medium as described by Miller, J. H., et al., *Experiments in Molecular Genetics*, Cold Spring Harbor Lab Press, Plainview, N.Y. (1972), the disclosure of which is incorporated herein by reference. Plasmid pHE2 was transformed by standard methods into *E. coli* JM109 and the cells were grown in TB medium [1.2% bactotryptone, 2.4% bactoyeast extract, 0.4% glycerol, 17 mM $KH_2PO_4$, 72 mM $K_2HPO_4$, and 100 µg of ampicillin (Sigma, St. Louis, Mo.) per ml] in a 20-liter Microferm fermenter (Model MF20) (New Brunswick Scientific, Edison, N.J.) at 30° C. until the cell density reached $1-2 \times 10^9$ cells per ml.

The expression of Hb A and Met-AP was induced by adding isopropyl β-thiogalactopyranoside to a concentration of 0.2 mM. The culture was then supplemented with 20 mg/liter hemin (Sigma) and 10 g/liter glucose, and the growth was continued for at least another 4 hours. The cells were then harvested by centrifugation and the cells were stored frozen in 100-gram portions at −80° C. until needed for purification.

Isolation and Purification of Recombinant Hbs

A.

The stored cells were suspended in lysis buffer (40 mM Tris HCl/1 mM benzamidine at 3 ml/g of cells), and sonicated in a Branson sonifier 450 (Branson, Danbury, Conn.) in an ice bath at 65–74 W twice for 4 minutes and then centrifuged at 40° C. for 45 minutes at 14,000 rpm in a Sorvall rotor GSA (E. I. duPont, Wilmington, Del.). The resulting supernatant was saturated with CO gas and the pH was adjusted to 8.0 with 1M Tris base. 10% polyethyleneimine (Sigma) (vol/vol) was added to a final concentration of 0.5% in order to precipitate out the nucleic acids. The mixture was then stirred for 15 minutes with a stream of CO gas blowing across the top and then centrifuged at 14,000 rpm for 45 minutes. The resulting supernatant was concentrated in a stirred-cell concentrator (Amicon, Inc., Beverly, Mass.), the pH was adjusted to 7.4 with dilute HCl, and the solution was dialyzed against 20 mM Tris HCl/0.1 mM triethylenetetraamine ("TETA") (Sigma), at pH 7.4 with several changes of buffer until the pH and conductivity of the supernatant matched those of the buffers.

Figure 2:
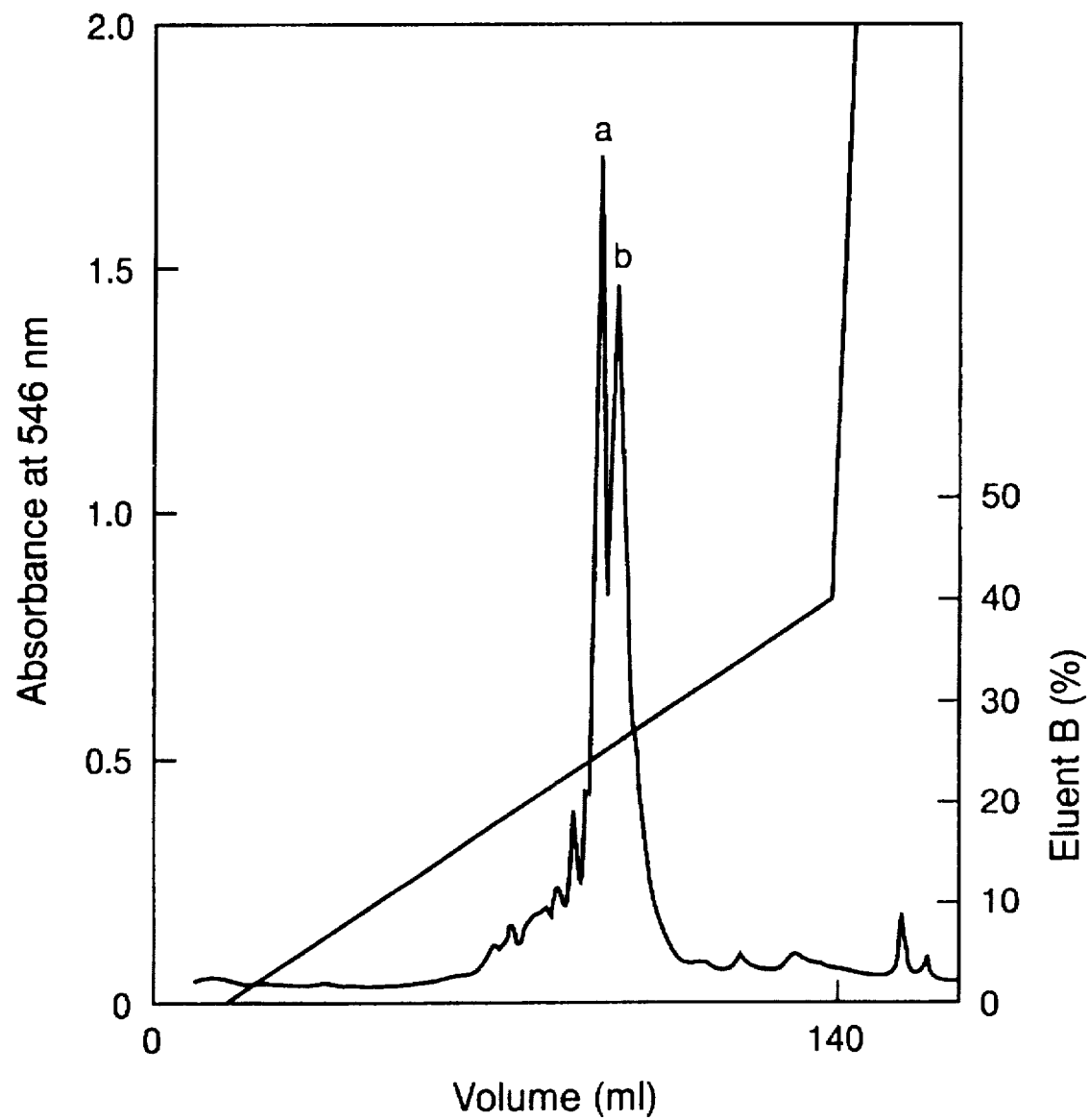
FIG. 2 shows a chromatographic elution profile from a MONO S column HR 10/10 (Pharmacia) of recombinant hemoglobins obtained from the partially purified sonicate of *E. coli* JM109 that was transformed with plasmid pHE2 showing peak a and peak b.

Three columns were used in the final purification process using a Pharmacia fast protein liquid chromatography ("FPLC") system. (1) The first column was a Q-SEPHAROSE fast flow column (Pharmacia anion exchanger) (5 cm×28 cm) with 20 mM Tris HCl/0.1 mM TETA, pH 7.4. About 80% of the unwanted protein was bound to the resin, while rHb A was eluted in the flow-through fraction in one major band. The eluent was concentrated and dialyzed against the start buffer for the next column. (2) The next column was a Q-SEPHAROSE fast flow column (2.6 cm×30 cm) with a gradient of 20 mM Tris-HCl/0.1 mM TETA, pH 8.3, to the same buffer with 160 mM NaCl. Hb A was eluted in one major peak. The peak tubes were then pooled, the pH was adjusted to 6.8 with 1M sodium monobasic phosphate, and the protein was concentrated and then dialyzed against the starting buffer for the third column. (3) The third column was MONO S column (Pharmacia cation exchanger, HR10/10) with a gradient of 10 mM sodium phosphate/0.1 mM EDTA, pH 6.8 (Eluent A), to 20 mM sodium phosphate/0.1 mM EDTA, pH 8.3 (Eluent B). Recombinant Hbs were eluted in two major peaks as shown in FIG. 2. These two peaks are referred to hereafter as "peak a" and "peak b" as shown in FIG. 2. Total protein concentration was determined by standard Lowry assays, and the Hb concentration was determined by using published extinction coefficients as described by Antonini, E., et al., *Hemoglobin and Myoglobin in Their Reactions with Ligands* (North Holland, Amsterdam) p. 19 (1971), the disclosure of which is incorporated herein by reference.

The separated α and β chains of Hb were then isolated and purified by the procedures of Bucci, E. *Methods Enzymol.* 76:97 (1981) and Waks, M., et al., *J. Biol. Chem.* 248:6462 (1973), the disclosures of which are incorporated herein by reference.

B.

Alternatively, an improved and simplified final purification process may preferably be carried out as follows.

After harvesting cells from the fermenter, the cell pellet was kept at −800° C. until ready for purification. All the isolation and purification procedures were carried out at 40° C., pH 8.0 and under CO to prevent oxidation of the heme-iron atoms of rHb.

Cell Lysate

The cell pellet from the −80° C. freezer was suspended in 40 mM Tris-HCl at pH 8.0/1 mM benzamide hydrochloride (Sigma) at 3 ml/g cell pellet. When the pellet completely thawed, freshly made lysozyme (ICN Biochemical Inc., Costa Mesa, Calif.) was added to give a final concentration of 1 mg lysozyme/g cell pellet and was stirred very gently for 15 minutes. $MgCl_2$, $MnCl_2$, and deoxyribonuclease I (ICN Biomedical Inc.) were added to give a final concentration of 10 mM, 1 mM, and 10 µg/ml, respectively. The lysate was then stirred gently for 15–30 minutes and then sonicated in a Branson sonifier 450 at setting 7 for 3 minutes 2–3 times or until the cells were completely lysed. The lysate was kept in an ice bath during this process to ensure that the temperature remained at 4°–8° C. The lysate was then centrifuged at 14,000 rpm for 45 minutes to eliminate cell membranes and other debris. The resulting supernatant was then gassed with CO for 15–20 minutes.

Concentration and Equilibration of Supernatant

The resulting supernatant was put into a flask in an ice bath to maintain the temperature at 4° C. The pH of the supernatant was then adjusted to 8.3 with 1M Tris-base (Sigma) and gassed with CO again for about 15 minutes. The supernatant was then put through a Minitan Ultrafiltration System (Millipore Corp., Bedford, Mass.), using 6 stacked membranes (nominal weight cutoff, 10,000 to 30,000 Daltons) to concentrate and equilibrate the supernatant. When the volume of the supernatant was down to about 100 ml, 400 ml of CO-gassed Q buffer (20 mM Tris-HCl/0.1 mM TETA, pH 8.3) was added and the concentration was continued. This process was repeated until the pH and the conductivity of the supernatant matched that of the Q buffer.

Purification Through Fast-Flow Q Column

A chromatography column (4 cm×21 cm) was packed with Q SEPHAROSE Fast Flow anionic-exchange resin (Pharmacia). The Q column was washed with the Q buffer until eluent from the column matched that of the buffer in pH and conductivity. The equilibrated sample was then loaded onto the column at about 15 ml/min. rHb binds to the column and nucleic acids and other proteins flow through. The column was washed with the Q buffer and the eluent was monitored at 260 nm until the optical density was at a minimum. The rHb was then eluted from the column with 20 mM Tris-HCl/0.1 mM TETA, pH 7.2. The rHb was collected and concentrated in an Amicon stirred-cell concentrator and equilibrated with 10 mM sodium phosphate/ 0.1 mM EDTA, pH 6.8 until the sample matched that of the buffer.

Purification Through MONO S Column

A MONO S column (HR 16/10) which uses cation-exchange resin (Pharmacia) was used as the final purification column. rHb was loaded at a maximum of 150–200 mg total protein. After the protein was loaded onto the column, the column was washed with one-column volume of the start buffer (eluent A10 mM sodium phosphate/0.1 mM EDTA, pH 6.8). The elution was started by first jumping to 15% end buffer (eluent B20 mM sodium phosphate/0.1 mM EDTA, pH 8.3) and a gradual gradient started from 15–30% eluent B in 200 ml.

After MONO S column purification, there were two fractions of rHb A, peak a and peak b, as described above. As discussed below, rHb A from peak a has the correct heme orientation. rHb A from peak b was then treated by an oxidation/reduction step as described in detail below in order to correct the conformation of the heme-iron atoms.

Forms of Hb

HbCO was prepared by passing a stream of CO gas through a $HbO_2$ or deoxy-Hb solution contained in a flask. This procedure was carried out inside a ventilated fume hood. Deoxy-Hb was usually prepared by converting HbCO or $HbO_2$ to the deoxygenated form in a rotary evaporator under $N_2$ gas at 4° C. as fully disclosed in Lindstrom, T. R., et al., *Proc. Natl. Acad. Sci. USA* 69:1707 (1972). Oxy-Hb was prepared by exposing deoxy-Hb solution to air or $O_2$ gas.

Protein Sequencing

Automated cycles of Edman degradation were performed with an Applied Biosystem gas/liquid-phase sequencer (Model 470/900A) that was equipped with an on-line phenylthiohydantoin-amino acid analyzer (Model 120A) as described by Hewick, R. M., et al., *J. Biol. Chem.* 256:7990 (1981), the disclosure of which is incorporated herein by reference.

SDS-Polyacrylamide Gel Electrophoresis

Figure 3:
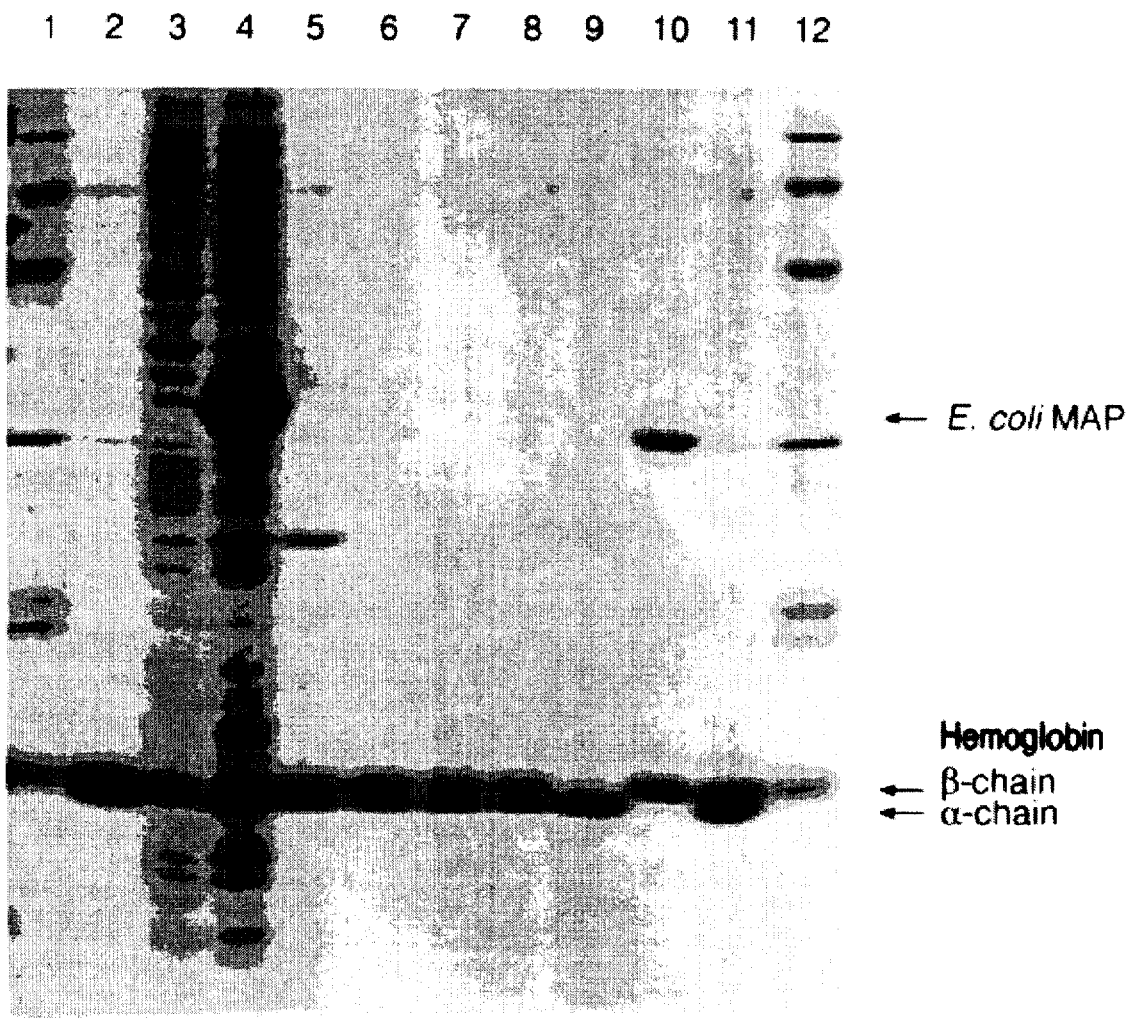
FIG. 3 is a photograph of a sodium dodecyl sulfate-polyacrylamide gel showing expression of rHb A in *E. coli* JM109 that was transformed with plasmid pHE2 (lanes 4–8), purified α and β chains of Hb A (lanes 9 and 10, respectively), native Hb A (lanes 2 and 11), and molecular weight markers (lanes 1 and 12). The band at approximately 33 kDa in lane 3 shows the expressed MAP in plasmid pHE2.

Sodium dodecyl sulfate-polyacrylamide gel electrophoresis "SDS-PAGE" was carried out using standard methods to monitor the efficiency of various columns (e.g., fast-flow Q column, MONO Q column, and MONO S column) to remove unwanted proteins and other materials from the cell sonicate. Lanes 1 and 12 contained molecular weight markers (KDa); lane 2 and 11 contained native Hb A; lane 3 contained a sample of the sonicate of *E. coli* JM109 harboring plasmid pDLIII-13e (human α- and β- globin genes are expressed); lane 4 contained a sample of the sonicate of *E. coli* JM109 harboring plasmid pHE2 (human α- and β-globin genes and *E. coli* MAP gene are coexpressed) as prepared above; lane 5 contained a sample of the protein fraction after the fast-flow Q column purification as described above; lane 6 contained a sample of the protein fraction after the MONO Q column purification (the resin for a MONO Q column is finer than that of a fast-flow Q column); lanes 7 and 8 contained protein fractions from peaks a and b, respectively after the MONO S column; lane 9 contained isolated α chain from Hb A; and lane 10 contained isolated β chain from Hb A. The results are shown in FIG. 3.

Mass Spectrometry

Hb samples subjected to mass spectrometry were dialyzed extensively against distilled $H_2O$ and then lyophilized. Immediately before analysis, the samples were dissolved in water to a concentration of 125 pmol of Hb per µl of $H_2O$ (7.8 mg/ml). Aliquots of these solutions were then diluted to give a final concentration of 10 pmol/µl of 50:50 water/acetonitrile containing 0.2% formic acid. Aliquots (10 µl) of these final solutions were introduced into the electrospray ion source at 5 µl/minute.

Figure 4A:
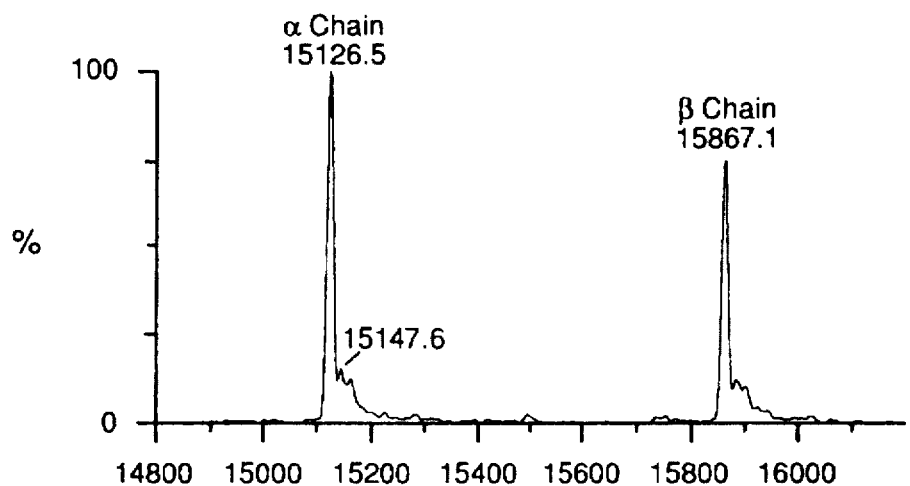
FIGS. 4A, 4B and 4C are electrospray mass spectra of Hb A and rHbs from peaks a and b obtained by MONO S column chromatography of the expressed Hbs from the sonicate of *E. coli* JM109 which was transformed with plasmid pHE2.
Figure 4B:
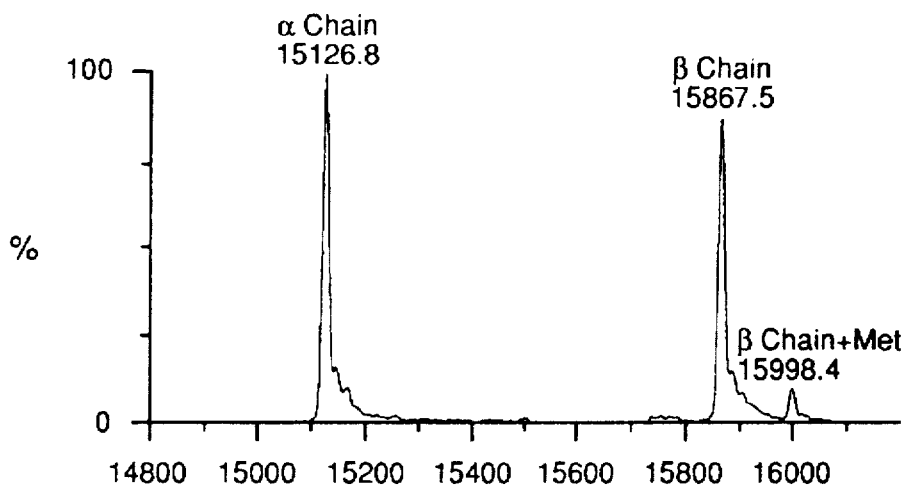
Figure 4C:
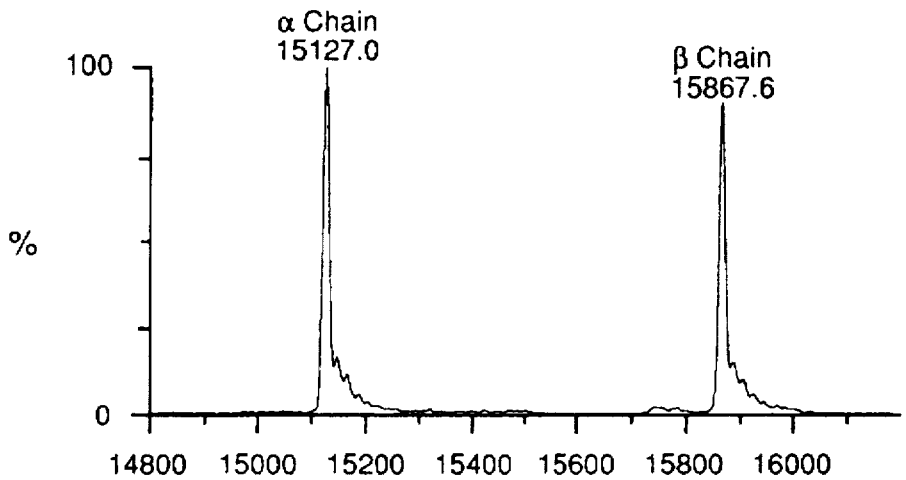

The electrospray analyses were performed on a VG Quattro-BQ (Fisons Instruments, VG Biotech, Altrincham, U.K.), a triple quadrupole instrument with a mass range for singly charged ions of 4000. Scanning was performed from m/z 980 in 10 seconds per scan. The data obtained from 20 scans were summed to give the final spectra. Mass scale calibration used the multiply charged ion peaks from the α chain ($M_r$=15,126.4) of Hb A as an external reference. The molecular weights calculated from the amino acid sequences of normal α chain, normal β chain, and β chain+ methionine are 15,126.4, 15,867.2, and 15,998.4, respectively. Such values are based on the following atomic weights of the elements: C=12.011; H=1.00794; N=14.00674; O=15.9994; and S=32.066, as reported by Commission on Atomic Weights and Isotopic Abundances, *Pure Appl. Chem.* 63:975 (1991), the disclosure of which is incorporated herein by reference. The resulting electrospray mass spectra are shown in FIGS. 4A–4C.

Conversion of Oxidation State of the Heme-Iron Atoms

In order to oxidize Hbs, in this case the CO form of Hb A and rHb A, to the $Fe^{+3}$ state, the concentration of Hb solution in 0.1M phosphate at pH 6.5 was determined. A 3-molar excess of $K_3Fe(CN)_6$ (Fisher Scientific) or other suitable oxidizing agent was added and the solution was stirred at room temperature for 1 hour. During this time the Hb solution changed from red to brownish color. The resulting oxidized Hb ($Fe^{+3}$) was put through a SEPHADEX G-25 (medium) column (Sigma) using 0.1M phosphate at pH 6.5 to remove excess $K_3Fe(CN)_6$ and left to stand for a few hours at room temperature.

The oxidized Hb ($Fe^{+3}$) was subsequently reduced by first preparing 0.1M phosphate at about pH 7.0 in a test tube, and deoxygenating the buffer by bubbling nitrogen through the buffer to remove the dissolved oxygen. In another tube, enough sodium dithionite (Fluka Chemie, Switzerland) was weighed out to give a 0.1 M solution of dithionite. The tube was then flushed with nitrogen to remove oxygen. The deoxy phosphate buffer was then anaerobically transferred to the deoxy dithionite to give a 0.1M final concentration. A stream of CO was blown across the top of (not bubbled through) the oxidized Hb solution. The deoxy dithionite buffer was added to the oxidized Hb solution until the color changed back to bright red. At this point the optical spectrum can be checked to ensure all the Hb ($Fe^{+3}$) is reduced to Hb ($Fe^{+2}$). A SEPHADEX G-25 column was equilibrated with the same CO gassed buffer that was used for reducing the Hb. The reduced Hb solution was then put through the SEPHADEX G-25 column using the same CO gassed buffer. The resulting oxidized/reduced Hb was then preferably purified through a FPLC MONO S column. The resulting oxidized, reduced, MONO S-purified rHb A was then converted to the carbonmonoxy or oxy form as desired as described above.

Other suitable oxidizing agents may be used to oxidize ferro-hemoglobin ($Fe^{+2}$) to ferri-Hb ($Fe^{+3}$) such as, for example, ferricyanide, copper, hydrogen peroxide, hydroxylamine, nitrites, hydrazines, thiols, arylamines or any compound with an electrical chemical potential ("$E_m$") greater than 0.14 volt. Other suitable reducing agents that may be used to reduce ferri-Hb ($Fe^{+3}$) to ferro-hemoglobin ($Fe^{+2}$) are: (i) for non-enzymatic reduction -dithionite, metabisulfite, cysteine, reduced glutathione, and ascorbic acid (in the presence of methylene blue); and (ii) for enzymatic reduction-cytochrome $b_5$ reductase, NADPH-flavin reductase, and any other compound with an $E_m$ less than 0.14 volt may be used. See, Bunn, H. F., et al., *Hemoglobin: Molecular, Genetic and Clinical Aspects* (Saunders, Philadelphia) pp. 634–662 (1986), the disclosure of which is incorporated herein by reference.

NMR Measurements $^1$H-NMR spectra were obtained on a Bruker AM-300 spectrometer that was operated at 300 MHz and at 29° C. All of the Hb samples were placed in 0.1M sodium phosphate buffer (in 100% $^1H_2O$) at pH 7.0, except for the ferric-Hb samples, which were at pH 6.5. The Hb concentration range was 0.8–1.4 mM. The water signal was suppressed by using the "jump-and-return" pulse sequence as reported by Plateau, P., et al., *J. Am. Chem. Soc.* 104:7310 (1982), the disclosure of which is incorporated herein by reference. The $^1$H-NMR spectra of the carbonmonoxy-Hb ("HbCO") and deoxy-Hb samples were obtained by using the proton decoupling coil of a 5-mm multinuclear probe (Bruker) with 90° C. pulses of 9.7 μseconds, spectral widths of 8 kHz (16 kHz for deoxy-Hb), and 8000-data points. Typically, 256 or 1024 scans were averaged to improve the signal-to-noise ratio. The $^1$H-NMR spectra of the ferri-Hb (met-Hb) samples were obtained by using a 5-mm selective proton probe (Bruker), with a 90° C. pulse width of 6 μseconds, repetition delay of 0.5 seconds, spectral width of 71.4 kHz, and 16,000-data points. Proton chemical shifts are referenced to the methyl proton resonance of the sodium salt of 2,2-dimethyl-2-silapentane-5 sulfonate ("DSS") indirectly by using the water signal, which signal occurs at 4.76 ppm downfield from that of DSS, as the internal reference. The resulting $^1$H-NMR spectra are shown in FIGS. 5–9.

Oxygen Binding of Hb A Samples

Figure 10A:
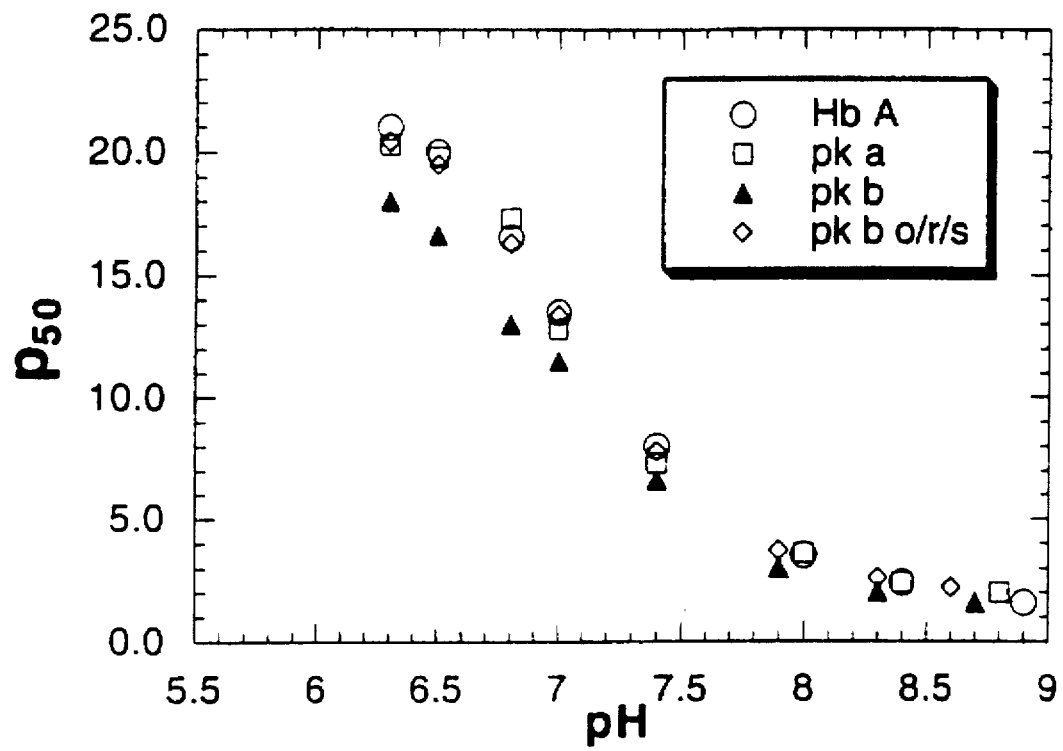
FIGS. 10A and 10B show $P_{50}$ (partial pressure of oxygen at 50% saturation) and $n_{max}$ (Hill coefficient) values, respectively for Hb A (○); rHb A from peak a (□); rHb A from peak b (▲); and rHb A from peak b that was oxidized, reduced, and run through a MONO S column ("o/r/ s") (◇).
Figure 10B:
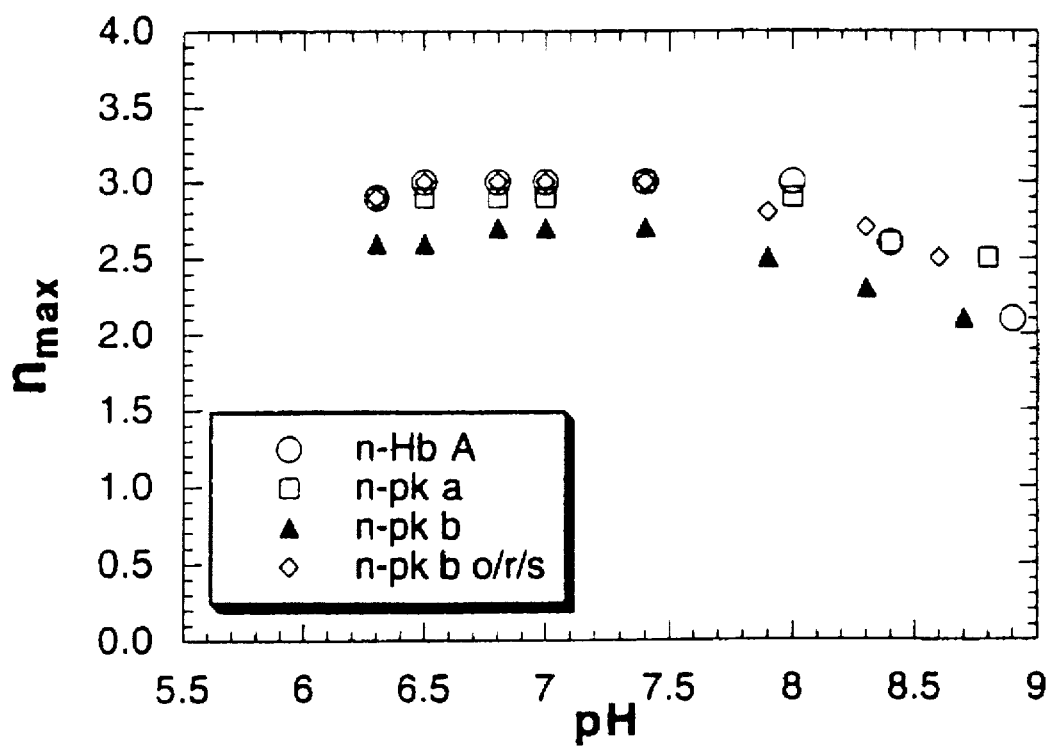

Oxygen-dissociation curves were measured by a Hemox-Analyzer (TCS Medical Products, Huntington Valley, PA) at 29° C. in 0.1M sodium phosphate buffer in the pH range of 6.0–8.3. The methemoglobin reductase system, described by Hayashi, A., et al., *Biochim. Biophys. Acta* 310:309 (1973), the disclosure of which is incorporated herein by reference, was added (30–60μl) to prevent the formation of ferri-Hb. Partial pressure at 50% oxygenation ($p_{50}$) and the Hill coefficient ($n_{max}$) were determined from each curve. The results of these studies are shown in FIGS. 10A and 10B, respectively.

III. RESULTS

As stated above, the MONO S chromatography of the expressed Hbs from the sonicate of *E. coli* JM109 which harbors plasmid pHE2 resulted in two major rHb components, peaks a and b as shown in FIG. 2. Each peak has a visible optical spectrum over the range of 350–700 nm in the carbonmonoxy form identical to that of Hb A (results not shown). The yield for the Hb peaks a and b was about 10–15% in terms of the total protein content after the polyethyleneimine precipitation step. A biochemical characterization of these two major components was then carried out as described above.

SDS-PAGE was carried out as described above. The results shown in FIG. 3 show the α chain and β chain of Hb A clearly present in the *E. coli* sonicates of lane 3 from expression plasmid pDLIII-13e and to an even greater extent, in the *E. coli* sonicates of lane 4 from expression plasmid pHE2. The two chains are also clearly present in all the FPLC protein fractions obtained as described above (lanes 5–8).

The electrospray mass spectrometry carried out as described above showed that for peak a, at least 98% of the α chain of the rHb A has the same mass, within experimental error of 0.005%, as that of the α chain of Hb A as seen in FIGS. 4A and 4B. However, there was a small component of up to approximately 5 to about 10% whose mass corresponds to that of normal β chain plus a methionine residue as shown in FIG. 4B. For peak b, both α and β chains had the correct masses with virtually undetectable, <2%, N-terminally added methionine as seen in FIG. 4C. All of these mass spectrometry results were confirmed by Edman degradation.

Figure 5A:
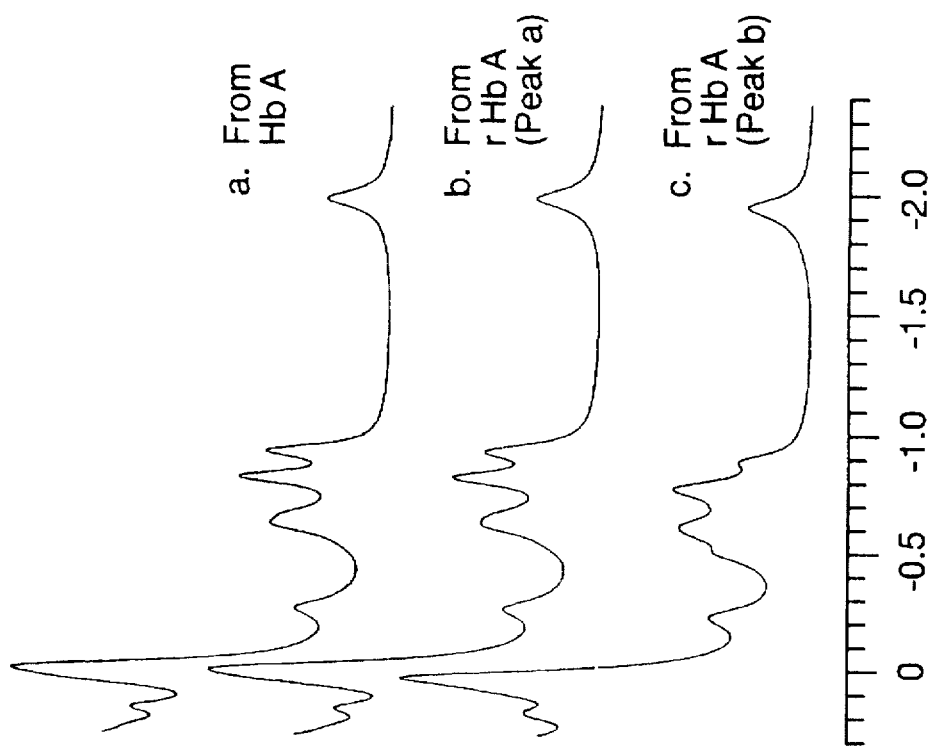
FIGS. 5A and 5B are $^1$H-NMR spectra showing ring-current shifted proton resonances of isolated α and β chains, respectively, both in CO form in 0.1M phosphate in $H_2O$ at 300 MHz, pH 7.0, and 29° C. In both figures, trace a is Hb A; trace b is rHb A from peak a; and trace c is rHb A from peak b.
Figure 5B:
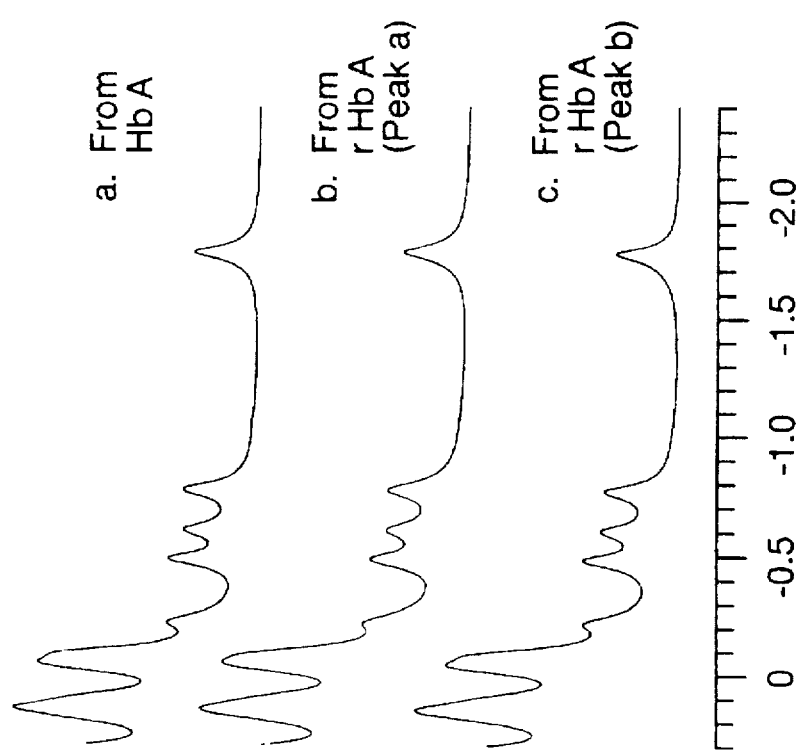

$^1$H-NMR spectroscopy has been shown to be an excellent tool to investigate the structural features of Hb A such as the tertiary structure, including the heme pockets, and the quaternary structure, namely, the subunit interfaces. See, Ho, C., *Adv. Protein Chem.* 43:153 (1992), the disclosure of which is incorporated herein by reference. The ring-current shifted $^1$H resonances of isolated α and β chains of Hb A and of rHbs from peaks a and b in the CO form are shown in FIGS. 5A (α chains) and 5B (β chains). Trace a in each Figure is native Hb A; trace b is rHb A from peak a; trace c is rHb A from peak b. As can be readily seen, there are no observable differences in the ring-current shifted $^1$H resonances among the isolated α chains from Hb A and rHb A from peaks a and b as seen in FIG. 5A. However, the ring-current shifted $^1$H resonances of the isolated β chains of rHbCO A from peak b (trace c) are different from those of Hb A and rHb A (traces A and B, respectively) and as seen in FIG. 5B. Thus, the conformation of the heme group in the β chain of the rHbCO A from peak b was altered, giving rise to the altered ring-current shifted $^1$H resonances in the spectra of the isolated β chains of FIG. 5A, trace c and of rHbCO A from peak b seen in FIG. 6, trace C.

Figure 6:
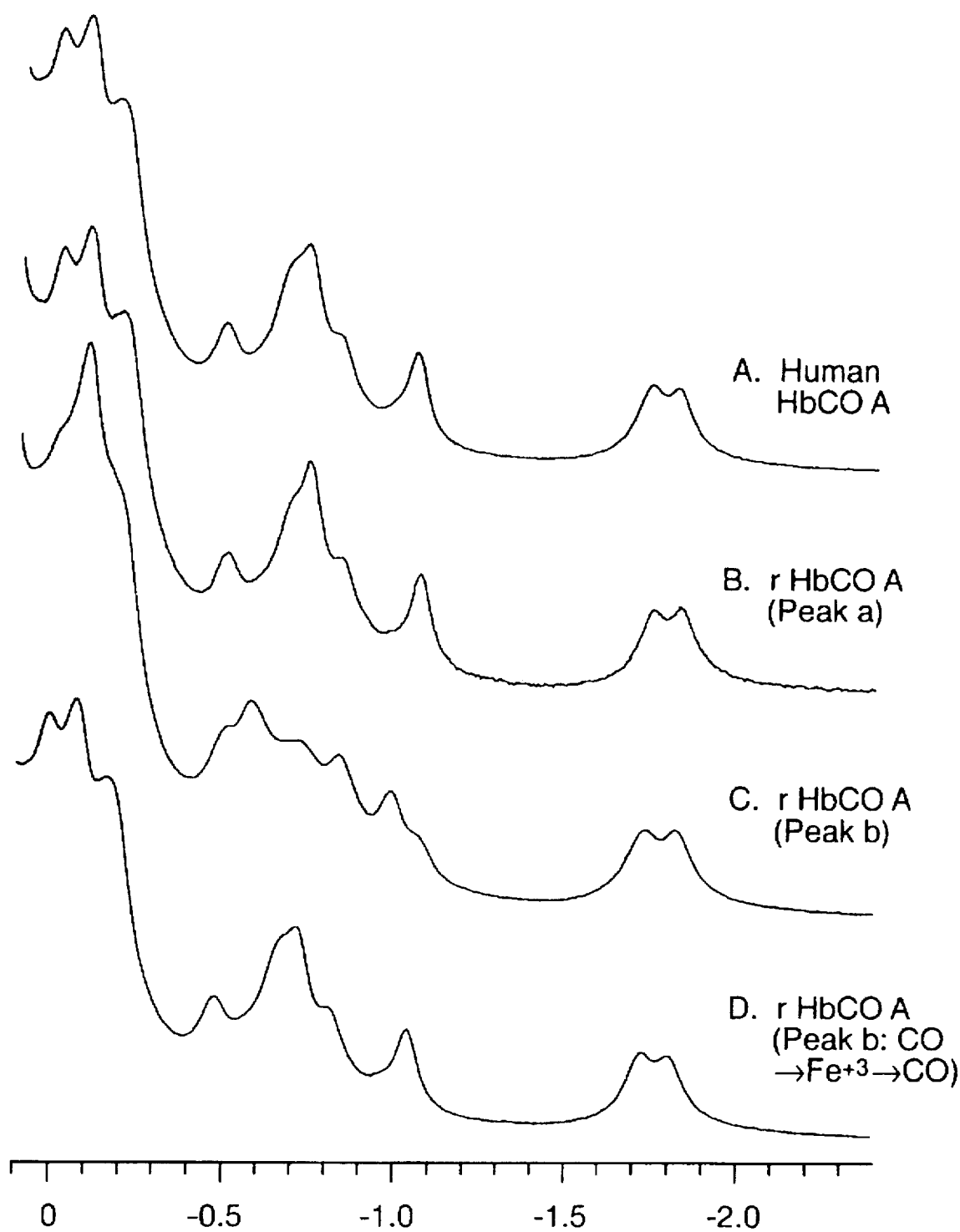
FIG. 6 is an $^1$H-NMR spectra showing ring-current shifted proton resonances of HbCO A and rHbCO A in 0.1M phosphate in $H_2O$ at 300 MHz, pH 7.0, and 29° C. Trace A is HbCO A; trace B is rHbCO A from peak a; trace C is rHbCO A from peak b; and trace D is rHbCO A from peak b, which was converted from the CO form to the $Fe^{+3}$ state and then back to the CO form.

FIG. 6 shows the ring-current shifted $^1$H resonances of Hb A and rHb A in the CO form. In FIG. 6 trace A is native HbCO A; trace B is rHBCO A from peak a; trace C is rHbCO A from peak b; trace D is rHbCO A from peak b which was converted to the $Fe^{+3}$ state, and then back to the CO form. The proton resonances over the region from 0 to −2.0 ppm arose from some of the protons of the amino acid residues situated in the heme pockets of the Hb molecule. The ring-current shifted $^1H$ resonances of rHbCO from peak a shown in FIG. 6, trace B, are identical to those of Hb A seen in FIG. 6, trace A, while those from peak b seen in FIG. 6, trace C, are distinctly different. There are additional $^1H$ resonances in rHbCO A from peak b that are not seen in HbCO A and there are also changes in the intensity in several of the resonances over the region from 0 to −1.1 ppm. These findings clearly suggest that there are alterations in the conformation of the heme pocket(s) of rHbCO A from peak b. The differences clearly shown in trace C disappear, however, when rHbCO A was oxidized to its $Fe^{+3}$ form and then reduced and converted to its CO form and purified through a MONO S column as described above (FIG. 6, trace D).

Figure 7:
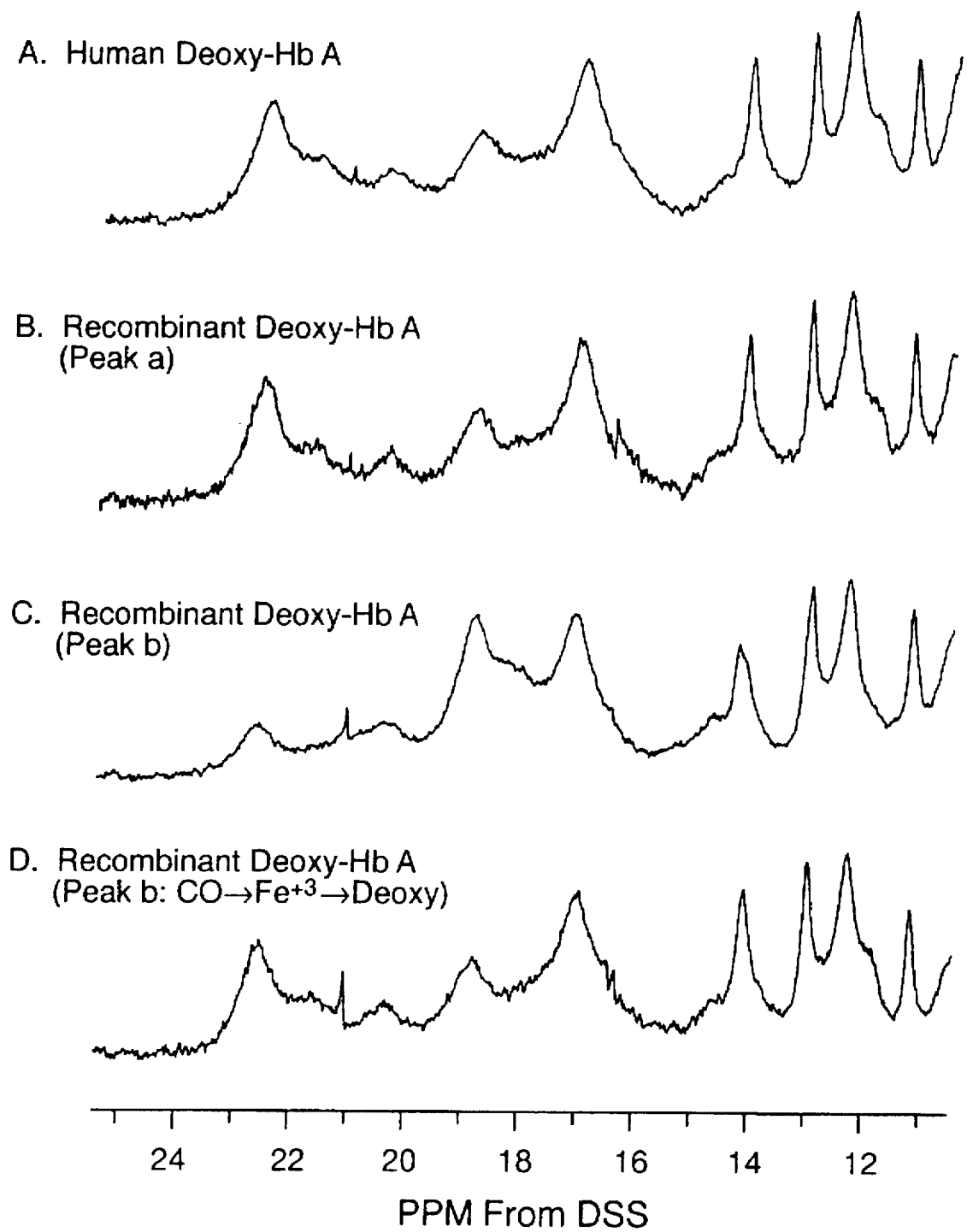
FIG. 7 are $^1$H-NMR spectra showing hyperfine-shifted and exchangeable proton resonances of deoxy-Hb and deoxy-rHbA in 0.1M phosphate in $H_2O$ at 300 MHz, pH 7.0, and 29° C. Trace A is deoxy-Hb A; trace B is deoxy-rHb A from peak a; trace C is deoxy-rHb A from peak b; and trace D is deoxy-rHb A from peak b, which was converted from the deoxy form to the $Fe^{+3}$ state and then back to the deoxy form. The spikes at approximately 16.5 and 21 ppm are instrumental artifacts.

The ferrous hyperfine-shifted and exchangeable proton resonances for Hb A from peaks a and b in the deoxy form are shown in FIG. 7. Trace A is native deoxy-Hb A; trace B is deoxy-rHb A from peak a; trace C is deoxy-rHb A from peak b; trace D is deoxy-rHb A from peak b that was converted to the CO form, then to the $Fe^{+3}$ form, then to the deoxy form. As shown in the figure, there are no differences in the ferrous hyperfine-shifted $^1H$ resonances (from 11 to 24 ppm) between deoxy-Hb A (trace A) and deoxy-rHb A (trace B) from peak a. Thus, there are no alterations in the heme pocket between these two Hbs in the deoxy state. However, there are alterations seen in the resonance patterns at approximately 22.5 and 18.7 ppm in deoxy-rHb A from peak b. These two resonances were assigned to protons that are associated with the β chains of deoxy-Hb A as reported by Takahashi, S., et al., *Biochemistry* 19:5196 (1980), the disclosure of which is incorporated herein by reference.

The exchangeable $^1H$ resonances over the spectral region from 11 to 14 ppm are excellent markers for the quaternary structure of a Hb molecule as reported by Fung, L. W.-M., et al., *Biochemistry* 14:2526 (1975), the disclosure of which is incorporated herein by reference. There is no observable difference seen in the resonance at approximately 14 ppm between deoxy-Hb A and deoxy-rHb A from peak a as seen in FIG. 7, traces A and B. However, the resonance at approximately 14 ppm in deoxy-rHb A from peak b (trace C) is altered somewhat, showing a sharper resonance plus a high-field shoulder as seen in FIG. 7. The alterations, however, virtually disappear in trace D where the deoxy-Hb A was oxidized, reduced, and converted back to the deoxy form, again indicating that the heme conformation is critical.

Figure 8:
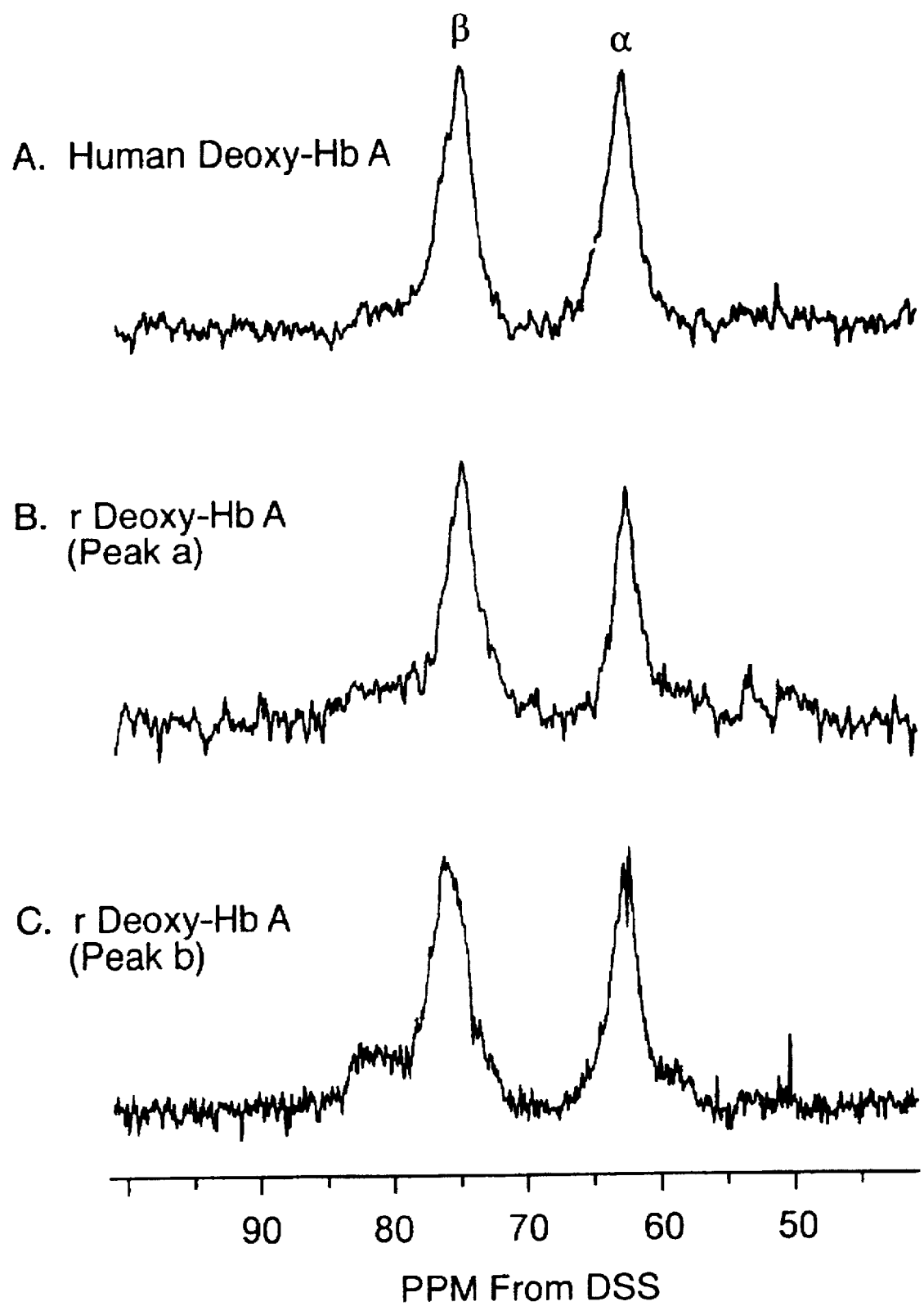
FIG. 8 are $^1$H-NMR spectra showing hyperfine-shifted $N_δ$-H proton resonances of proximal histidine residues of deoxy-rHb A and deoxy-Hb A in 0.1M phosphate in $H_2O$ at 300 MHz, pH 7.0, and 29° C. Trace A is deoxy-Hb A; trace B is deoxy-rHb A from peak a; and trace C is deoxy-rHb A from peak b. The spikes at approximately 51 and 56 ppm are instrumental artifacts.

The results of the investigation of the very low-field $^1H$ resonances of Hb A and rHb A for peaks a and b in the deoxy form are shown in FIG. 8. Trace A is native deoxy-Hb A; trace B is deoxy-rHb A from peak a; and trace C is deoxy-rHb A from peak b. The resonance at approximately 63 ppm was assigned to the hyperfine-shifted $N_\delta H$-exchangeable proton of the proximal histidine residue of the α chain of deoxy-Hb A and the one at approximately 77 ppm was assigned to the corresponding residue of the β chain of deoxy-Hb A. See, Takahashi, S., et al., *Biochemistry* 19:5196 (1980) and La Mar. G. N., et al., *Biochem. Biophys. Res. Commun.* 96:1172 (1980), the disclosures of which are incorporated herein by reference.

FIG. 8 again shows no observable difference in the two resonances from Hb A and rHb A from peak a in traces A and B, respectively. However, there are two observable differences between the resonances from rHb A from peak b (trace C) and Hb A (trace A): (1) the approximately 77 ppm resonance is shifted downfield by about 1 ppm as compared with that of Hb A; and (2) there is a shoulder at approximately 82 ppm in the spectrum of rHb A from peak b, which is not seen in Hb A as shown in FIG. 8, traces A and C.

Figure 9A:
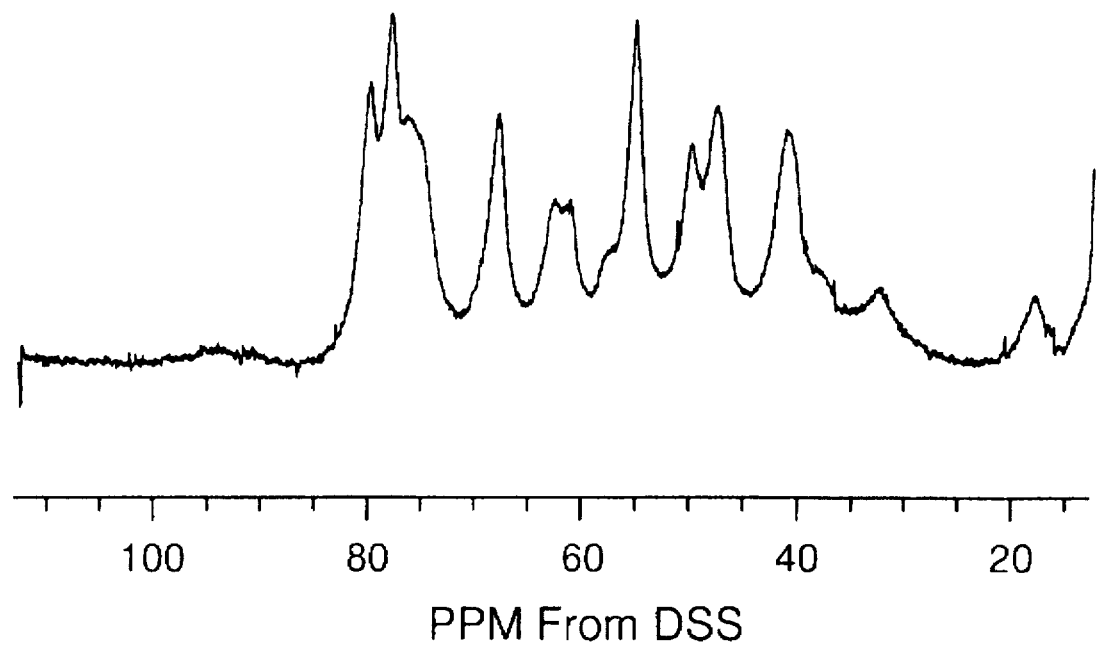
FIGS. 9A and 9B are $^1$H-NMR spectra showing hyperfine-shifted proton resonances of Hb A in its $Fe^{+3}$ state and rHb A from peak b in its $Fe^{+3}$ state, respectively, in 0.1M phosphate in $H_2O$ at pH 6.5 and 29° C.
Figure 9B:
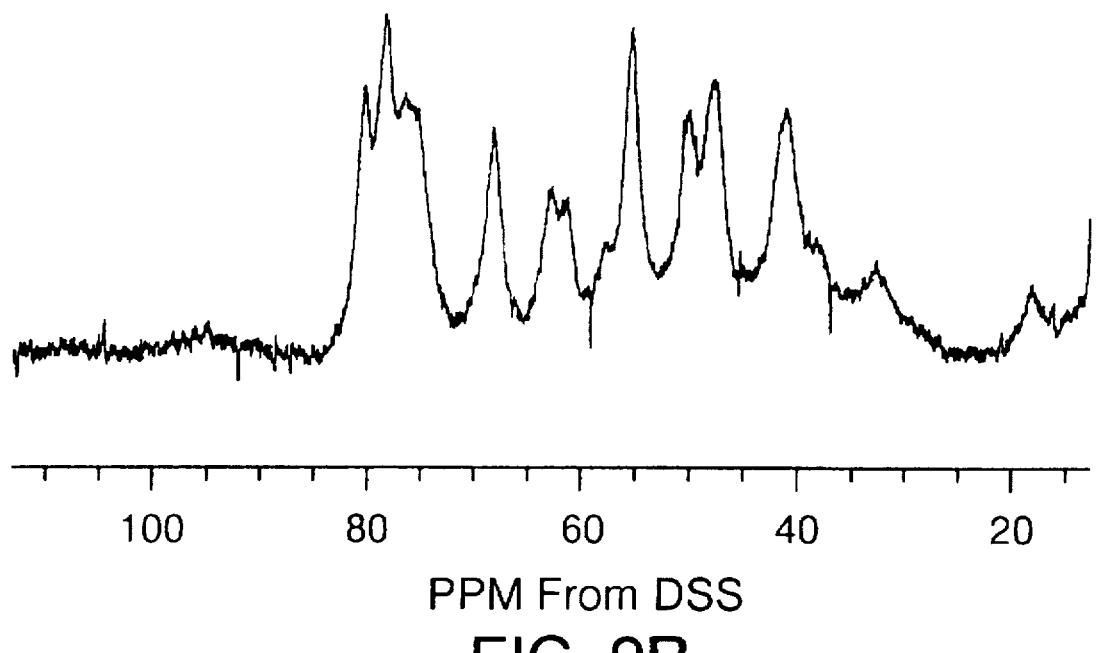

The possibility of converting the abnormal $^1H$ resonances seen in the β chain from peak b of rHb A to those seen in Hb A by first oxidizing rHbCO A to the ferric form and then reducing it to the ferrous form and then finally converting it back to the CO or oxy form was further investigated as described above. As seen in FIG. 9, there was no observable difference in the high-spin ferric hyperfine-shifted $^1H$ resonances between Hb A and rHb A from peak b in the ferric ($Fe^{+3}$) state over the spectral region from 15 to 85 ppm downfield from DSS as measured in 0.1M phosphate in $H_2O$ at pH 6.5 and 29° C. Such findings indicate that the heme group in its original, reduced state is somewhat not correctly oriented, but that appropriate correction is achieved by oxidation to the $Fe^{+3}$ state.

The oxygen-binding properties of the rHbs in peaks a and b were investigated as described above. The oxygen binding properties of Hb A (○), rHb A from peak a (□), rHb A from peak b (▲), and rHb A from peak b that was oxidized, then reduced, then purified through a MONO S column as described above (oxidized/reduced/purified through a MONO S column "o/r/s") (◇) were determined. FIG. 10A shows $p_{50}$ values in 0.1M phosphate at 29° C.; FIG. 10B shows the Hill coefficient ($n_{max}$) for the same Hbs. As can be seen, the Hb components from the two peaks bound $O_2$ cooperatively with a Hill coefficient similar to that of Hb A in 0.1M phosphate at 29° C. From pH 6.8 to 8.2, the $p_{50}$ values of Hb A and rHb A were very similar. At pH's below 6.8, the values of Hb A and rHb A from peak a were very similar, but rHb A from peak b consistently had somewhat lower $p_{50}$ and $n_{max}$ values. These results show that the rHb A from peak b does not have the same $p_{50}$ or $n_{max}$ values, whereas the rHb A from peak b that was oxidized, reduced, and run through a MONO S column has virtually the same properties as native Hb A.

Such results again indicate that the conformation of the heme pockets of rHb A from peak b was converted to that of Hb A via its conversion to the ferric state. As discussed above, the $^1$H-NMR spectra of the "reconverted" Hb in both the CO and deoxy forms confirm this. Traces D in FIGS. 6 and 7 show that the $^1$H-NMR spectra of the "reconverted" rHb A from peak b are indistinguishable from those of native Hb A and rHb A from peak a as seen in traces A and B in FIGS. 6 and 7.

The foregoing demonstrates that insertion of heme groups is not always correctly carried out by the expression system of the present invention, but that the proper heme group orientation can be attained by the present invention's method of altering the oxidation state of the iron atoms. This implies that many recombinant proteins may not have proper insertion or orientation of heme or other prosthetic groups and that the present invention can be used to convert such recombinantly produced proteins to their native conformations.

The foregoing shows that the coexpression of *E. coli* MAP in pHE2 effectively removed the N-terminal methionines of the expressed α- and β-globins. The $^1$H-NMR results also showed a clear alteration of the heme conformation in the β chain of rHb A from peak b, implying that the heme may not always be properly inserted in *E. coli*. However, when the heme iron was oxidized to the ferric state, the heme rearranged itself to its native, correct conformation as in Hb A. Thus, the present invention provides procedures for producing recombinant hemoglobin with the correct structural and functional properties from expression in *E. coli* via (1) the expression plasmid pHE2, and (2) the procedure described herein to convert the incorrect conformation of the β subunit to the correct conformation. Thus, it is now possible to prepare not only recombinant hemoglobin with essentially the same properties as native hemoglobin, but also, mutant hemoglobins can now be prepared that have a wide variety of uses.

Although the invention has been described in detail for the purposes of illustration, it is to be understood that such detail is solely for that purpose and that variations can be made therein by those skilled in the art without departing form the spirit and scope of the invention except as it may be limited by the claims.

We claim:

1. A method for producing recombinant human normal adult hemoglobin (rHb A) that has the same amino acid sequence and heme conformation as native Hb A, comprising:

growing recombinant cells in a growth medium, said cells being a microorganism or cell culture transformed with an expression vector containing DNA encoding human α- and β-globin genes and the methionine aminopeptidase gene under the control of separate tac promoters;

simultaneously expressing said DNA, thereby producing recombinant hemoglobins that are substantially free of N-terminal methionine;

thereafter purifying said recombinant hemoglobins to obtain two major rHb A components wherein the rHb A of the first component has essentially the same structural and functional properties as those of native Hb A, except that the β subunit of said rHb A contains between about 5 to 10% of amino-terminal methionine residues resulting from said expression and the rHb A of the second component has the same amino acid composition as native Hb A, but whose structural and functional properties differ from those of native Hb A; and converting the heme group conformation of the rHb A that comprises the second component to the native heme group conformation by oxidizing said rHb A to the $Fe^{+3}$ state, and then reducing said oxidized rHb A to the $Fe^{+2}$ state and thereafter purifying said reduced rHb A.

2. The method of claim 1, wherein said expression vector is pHE2.

3. The method of claim 1, wherein said microorganism or cell culture is *E. coli*.

4. The method of claim 1, wherein said purification is carried out by fast protein liquid chromatography.

5. The method of claim 1 wherein said oxidation is carried out with ferricyanide.

6. The method of claim 1 wherein said reduction is carried out with dithionite.

7. The method of claim 1, further comprising the step of purifying said reduced rHb A through a chromatography column.

8. Plasmid pHE2.

9. A recombinant DNA expression plasmid, comprising expressible human α- and β-globin genes and Met-AP gene from *E. coli* arranged in tandem under the control of separate tac promoters, said sequences being expressed separately for said human α- and β-globin genes and said Met-AP gene and incorporating heme to form rHb A with essentially the same amino acid sequence and heme conformation as native Hb A after oxidation and reduction of the second rHb A component obtained by fast protein liquid chromatography of the rHb A expressed by said plasmid.

* * * * *